US006093742A

United States Patent [19]
Salituro et al.

[11] Patent Number: 6,093,742
[45] Date of Patent: Jul. 25, 2000

[54] INHIBITORS OF P38

[75] Inventors: Francesco Gerald Salituro, Marlborough; Guy W. Bemis, Arlington; Jeremy Green, Burlington, all of Mass.; James L. Kofron, Bristol, Wis.

[73] Assignee: Vertex Pharmaceuticals, Inc., Cambridge, Mass.

[21] Appl. No.: 08/884,160

[22] Filed: Jun. 27, 1997

[51] Int. Cl.$^7$ .......................... A61K 31/17; C07C 275/28
[52] U.S. Cl. ............... 514/596; 564/48; 564/49; 564/50; 564/26; 514/585; 514/597; 514/598
[58] Field of Search ........................ 514/596, 597, 514/598, 585; 564/48, 49, 50, 52, 53, 26

[56] References Cited

U.S. PATENT DOCUMENTS

| 5,716,972 | 2/1998 | Adams et al. | 514/341 |
| 5,807,876 | 9/1998 | Armistead | 514/374 |
| 5,843,904 | 12/1998 | Bemis et al. | 514/18 |

FOREIGN PATENT DOCUMENTS

| WO 95/31451 | 11/1995 | WIPO . |
| WO 96/40673 | 12/1996 | WIPO . |
| WO 97/40028 | 10/1997 | WIPO . |
| WO 97/49399 | 12/1997 | WIPO . |
| WO 97/49400 | 12/1997 | WIPO . |

OTHER PUBLICATIONS

Blum–Degen et al., Interleukin–1B and Interleukin–6 are Elevated in the Cerebrospinal Fluid of Alzheimer's and de novo Parkinson's Disease Patients, Neurosci. Lett. 202, 17–20 (1995).
Kumar et al., Activation of the HIV–1 Long Terminal Repeat by Cytokines and Environmental Stress Requires an Active CSBP/p38 MAP Kinase, J. Biol. Chem. 271, 30864–69 (1996).

*Primary Examiner*—John Kight
*Assistant Examiner*—Charanjit S. Awlakh
*Attorney, Agent, or Firm*—Fish & Neave; James F. Haley, Jr.; Karen E. Brown

[57] ABSTRACT

The present invention relates to inhibitors of p38, a mammalian protein kinase involved in cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

22 Claims, No Drawings

INHIBITORS OF P38

TECHNICAL FIELD OF INVENTION

The present invention relates to inhibitors of p38, a mammalian protein kinase involved cell proliferation, cell death and response to extracellular stimuli. The invention also relates to methods for producing these inhibitors. The invention also provides pharmaceutical compositions comprising the inhibitors of the invention and methods of utilizing those compositions in the treatment and prevention of various disorders.

BACKGROUND OF THE INVENTION

Protein kinases are involved in various cellular responses to extracellular signals. Recently, a family of mitogen-activated protein kinases (MAPK) have been discovered. Members of this family are Ser/Thr kinases that activate their substrates by phosphorylation [B. Stein et al., *Ann. Rep. Med. Chem.*, 31, pp. 289–98 (1996)]. MAPKs are themselves activated by a variety of signals including growth factors, cytokines, UV radiation, and stress-inducing agents.

One particularly interesting MAPK is p38. p38, also known as cytokine suppressive anti-inflammatory drug binding protein (CSBP) and RK, was isolated from murine pre-B cells that were transfected with the lipopolysaccharide (LPS) receptor CD14 and induced with LPS. p38 has since been isolated and sequenced, as has the cDNA encoding it in humans and mouse. Activation of p38 has been observed in cells stimulated by stresses, such as treatment of lipopolysaccharides (LPS), UV, anisomycin, or osmotic shock, and by cytokines, such as IL-1 and TNF.

Inhibition of p38 kinase leads to a blockade on the production of both IL-1 and TNF. IL-1 and TNF stimulate the production of other proinflammatory cytokines such as IL-6 and IL-8 and have been implicated in acute and chronic inflammatory diseases and in post-menopausal osteoporosis [R. B. Kimble et al., *Endocrinol.*, 136, pp. 3054–61 (1995)].

Based upon this finding it is believed that p38, along with other MAPKs, have a role in mediating cellular response to inflammatory stimuli, such as leukocyte accumulation, macrophage/monocyte activation, tissue resorption, fever, acute phase responses and neutrophilia. In addition, MAPKs, such as p38, have been implicated in cancer, thrombin-induced platelet aggregation, immunodeficiency disorders, autoimmune diseases, cell death, allergies, osteoporosis and neurodegenerative disorders. Inhibitors of p38 have also been implicated in the area of pain management through inhibition of prostaglandin endoperoxide synthase-2 induction. Other diseases associated with Il-1, IL-6, IL-8 or TNF overproduction are set forth in WO 96/21654.

Others have already begun trying to develop drugs that specifically inhibit MAPKs. For example, PCT publication WO 95/31451 describes pyrazole compounds that inhibit MAPKs, and in particular p38. However, the efficacy of these inhibitors in vivo is still being investigated.

Accordingly, there is still a great need to develop other potent, p38-specific inhibitors that are useful in treating various conditions associated with p38 activation.

SUMMARY OF THE INVENTION

The present invention solves this problem by providing compounds which demonstrate strong and specific inhibition of p38.

These compounds have the general formula:

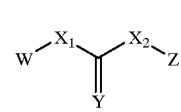

(I)

wherein:
W is a saturated, partially saturated or aromatic monocyclic or bicyclic ring system containing 0–4 heteroatoms selected from N, O, and S, wherein W optionally comprises up to 4 substituents independently selected from $R^1$ and $R^4$;
  wherein $R^1$ is halogen, $OR^3$, $NO_2$, $NH_2$, $N(R^3)_2$, $CO_2R^3$, $CON(R^3)_2$, $COR^3$, $NHCOR^3$, $SO_2NR^3$, $CN$, $SR^3$, 1,2-methyleneoxy, 1,2-ethylenedioxy or $CF_3$;
Y is O, S or NH;
$X_1$ and $X_2$ are independently selected from O, S or $NR^2$;
  wherein $R^2$ is selected from H or $C_1$–$C_6$ straight or branched alkyl, $C_2$–$C_6$ straight or branched alkenyl or alkynyl, wherein $R^2$ is optionally substituted with —OH, —N($R^3$)$_2$, —Z, —$CO_2R^3$ or —CO—N($R^3$)$_2$;
  $R^3$ is selected from H, $C_1$–$C_6$ straight or branched alkyl, $C_2$–$C_6$ straight or branched alkenyl or alkynyl, or $C_{6-20}$ aryl wherein $R^3$ optionally contains up to 4 substituents selected from halo, —OH, —$OR^4$, —$NO_2$, —$NH_2$, —$N(R^4)_2$, —$CO_2R^4$, —CO—N($R^4$)$_2$, —Z, —CN, —$SR^4$, $CF_3$ or —$SO_2NR^4$;
  $R^4$ is independently H, ($C_1$–$C_6$)-straight or branched alkyl, ($C_2$–$C_6$)-straight or branched alkenyl or alkynyl;
Z is selected from $C_3$–$C_7$-cycloalkyl, $C_5$–$C_7$-cycloalkenyl or aromatic or non-aromatic 5–7 membered monocyclic or bicyclic ring containing 0–4 heteroatoms selected from N, O and S, wherein Z optionally comprises up to 4 substituents independently selected from $R^1$ and $R^4$.

In another embodiment, the invention provides pharmaceutical compositions comprising the p38 inhibitors of this invention. These compositions may be utilized in methods for treating or preventing a variety of disorders, such as cancer, inflammatory diseases, autoimmune diseases, destructive bone disorders, proliferative disorders, infectious diseases, viral diseases and neurodegenerative diseases. These compositions are also useful in methods for preventing cell death and hyperplasia and therefore may be used to treat or prevent reperfusion/ischemia in stroke, heart attacks, organ hypoxia. The compositions are also useful in methods for preventing thrombin-induced platelet aggregation. Each of these above-described methods is also part of the present invention.

DETAILED DESCRIPTION OF THE INVENTION

The present invention provides inhibitors of p38 having the general formula:

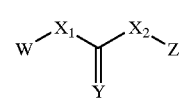

(I)

wherein W is a saturated, partially saturated or an aromatic monocyclic or bicyclic ring system containing 0–4 heteroatoms independently selected from N, O, and S, wherein W optionally comprises up to 4 substituents independently selected from $R^1$ and $R^4$.

$R^1$ is selected from halogen, $OR^3$, $NO_2$, $NH_2$, $N(R^3)_2$, $CO_2R^3$, $CON(R^3)_2$, $COR^3$, $NHCOR^3$, $SO_2NR^3$; CN, $SR^3$, 1,2-methyleneoxy, 1,2-ethylenedioxy or $CF_3$.

Y is O, S or NH.

$X_1$ and $X_2$ are independently selected from O, S or $NR^2$.

wherein $R^2$ is selected from H or $C_1$–$C_6$ straight or branched alkyl, $C_2$–$C_6$ straight or branched alkenyl or alkynyl, wherein $R^2$ is optionally substituted with —OH, —$N(R^3)_2$, —Z, —$CO_2R^3$ or —CO—$N(R^3)_2$.

$R^3$ is selected from H, $C_1$–$C_6$ straight or branched alkyl, $C_2$–$C_6$ straight or branched alkenyl or alkynyl or $C_{6-20}$ aryl, wherein $R^3$ optionally contains up to 4 substituents selected from halo, —OH, —$OR^4$, —$NO_2$, —$NH_2$, —$N(R^4)_2$, —$CO_2R^4$, —CO—$N(R^4)_2$, —Z, —CN, —$SR^4$, $CF_3$ or —$SO_2NR^4$.

$R^4$ is independently H, $(C_1$–$C_6)$-straight or branched alkyl, $(C_2$–$C_6)$-straight or branched alkenyl or alkynyl.

Z is selected from $C_3$–$C_7$-cycloalkyl, $C_5$–$C_7$-cycloalkenyl or aromatic or non-aromatic 5–7 membered monocyclic or bicyclic ring systems containing 0–4 heteroatoms selected from N, O and S, wherein Z optionally comprises up to 4 substituents independently selected from $R^1$ and $R^4$.

According to a preferred embodiment, W is an aromatic or non-aromatic 5–7 membered monocyclic ring containing up to 3 heteroatoms selected from O, S and N, and optionally containing up to 3 substituents selected from halo, $OR^3$, $NO_2$, $NH_2$, $N(R^3)_2$, $CO_2R^3$, $CON(R^3)_2$, $COR^3$, $NHCOR^3$, $SO_2NR^3$, CN, $SR^3$, 1,2-methyleneoxy, 1,2-ethylenedioxy, $CF_3$, $(C_1$–$C_6)$-straight or branched alkyl, $(C_2$–$C_6)$-straight or branched alkenyl or alkynyl.

According to a more preferred embodiment, W phenyl or pyridyl, each containing up to 3 substituents selected from halo, $OR^3$, $NO_2$, $NH_2$, $N(R^3)_2$, $CO_2R^3$, $CON(R^3)_2$, $COR^3$, $NHCOR^3$, $SO_2NR^3$, CN, $SR^3$, 1,2-methyleneoxy, 1,2-ethylenedioxy, $CF_3$ or $(C_1$–$C_6)$-straight or branched alkyl.

Some specific examples of the preferred W are:

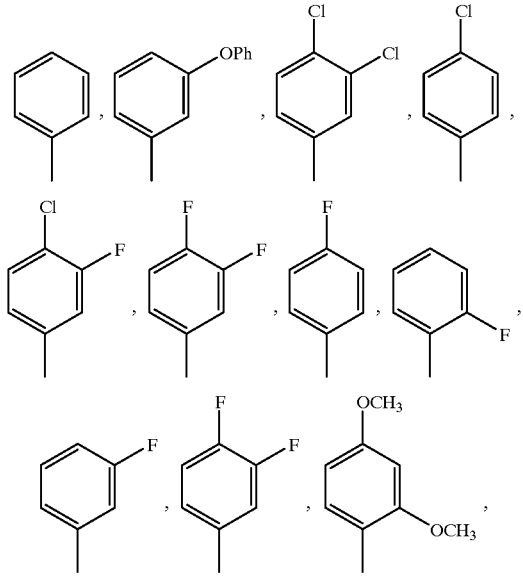

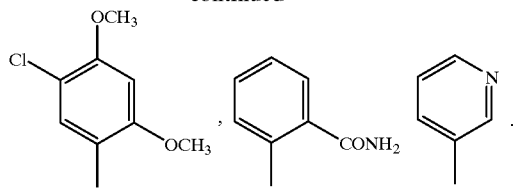

Most preferably, W is phenyl, 3,4-dichlorophenyl, 2-fluorophenyl or 2-amidophenyl.

According to a preferred embodiment, Z is a 5–7 membered aromatic or non aromatic ring system, optionally containing up to 4 heteroatoms independently selected from N, O and S, wherein Z optionally comprises up to 4 substituents selected from halo, $OR^3$, $NO_2$, $NH_2$, $N(R^3)_2$, $CO_2R^3$, $CON(R^3)_2$, $COR^3$, $NHCOR^3$, $SO_2NR^3$, CN, $SR^3$, 1,2-methyleneoxy, 1,2-ethylenedioxy, $CF_3$, $(C_1$–$C_6)$-straight or branched alkyl, $(C_2$–$C_6)$-straight or branched alkenyl or alkynyl.

According to a more preferred embodiment, Z is selected from phenyl or pyridyl, each containing up to 3 substituents selected from halo, $OR^3$, $NO_2$, $NH_2$, $N(R^3)_2$, $CO_2R^3$, $CON(R^3)_2$, $COR^3$, $NHCOR^3$, $SO_2NR^3$, CN, $SR^3$, 1,2-methyleneoxy, 1,2-ethylenedioxy, $CF_3$ or $(C_1$–$C_6)$-straight or branched alkyl.

According to an even more preferred embodiment, Z is a 2,4,5-trisubstituted phenyl or a 3,4-disubstituted phenyl, wherein the substituents are selected from halo, $OR^3$, $NO_2$, $NH_2$, $N(R^3)_2$, $CO_2R^3$, $CON(R^3)_2$, $COR^3$, $NHCOR^3$, $SO_2NR^3$, CN, $SR^3$, 1,2-methyleneoxy, 1,2-ethylenedioxy, $CF_3$ or $(C_1$–$C_6)$-straight or branched alkyl.

Some specific examples of preferred Z are:

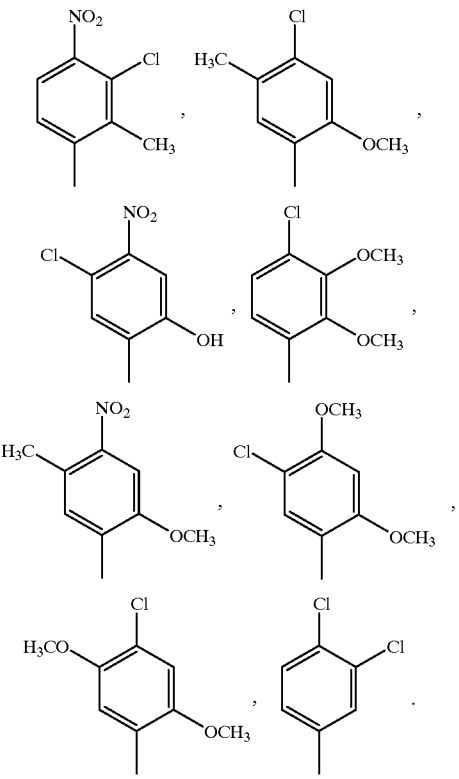

Most preferred are compounds wherein Z is 4-chloro-2-methyl-5-nitro-phenyl, 4-chloro-2-methoxy-5-methylphenyl, 5-chloro-2-hydroxy-4-nitrophenyl, 2,4-dimethoxy-5-chlorophenyl, 2-methoxy-4-nitro-5-methylphenyl, 2,5-dimethoxy-4-chlorophenyl, 3,4-dichlorophenyl.

According to another preferred embodiment, Y is C or S. Most preferably, Y is O.

According to another preferred embodiment, $X_1$ and $X_2$ are independently O or $NR^2$. More preferably, $X_1$ and $X_2$ are both $NR^2$. Most preferably, $X_1$ and $X_2$ are both NH.

Some specific inhibitors of this invention are set forth in Table 1 below.

TABLE 1

| compound number | Structure |
|---|---|
| 1 | |
| 2 | |
| 3 | |
| 4 | |
| 5 | |
| 6 | |
| 7 | |
| 8 | |
| 9 | |
| 10 | |

TABLE 1-continued

| compound number | Structure |
| --- | --- |
| 11 | |
| 12 | |
| 13 | |
| 14 | |
| 15 | |
| 16 | |
| 17 | |
| 18 | |
| 19 | |
| 20 | |

TABLE 1-continued

| compound number | Structure |
|---|---|
| 21 | [structure: 2-(phenoxycarbonyl)phenyl urea with 5-chloro-2,4-dimethoxyphenyl] |
| 22 | [structure: 3-phenoxyphenyl urea with 5-chloro-2,4-dimethoxyphenyl] |
| 23 | [structure: 4-(dimethylamino)phenyl urea with 5-chloro-2,4-dimethoxyphenyl] |
| 24 | [structure: 3,4-dichlorophenyl urea with 5-chloro-2,4-dimethoxyphenyl] |
| 25 | [structure: phenyl urea with 5-chloro-2,4-dimethoxyphenyl] |
| 26 | [structure: 2,3-dihydro-1,4-benzodioxin-6-yl urea with 5-chloro-2,4-dimethoxyphenyl] |
| 27 | [structure: 4-carboxyphenyl urea with 5-chloro-2,4-dimethoxyphenyl] |
| 28 | [structure: 2-hydroxyphenyl urea with 5-chloro-2,4-dimethoxyphenyl] |

TABLE 1-continued
| compound number | Structure |
|---|---|
| 29 | 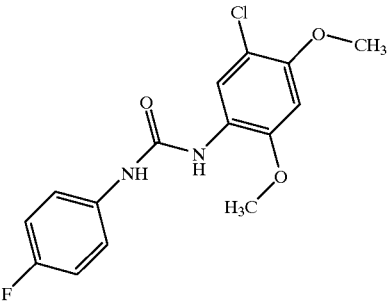 |
| 30 | 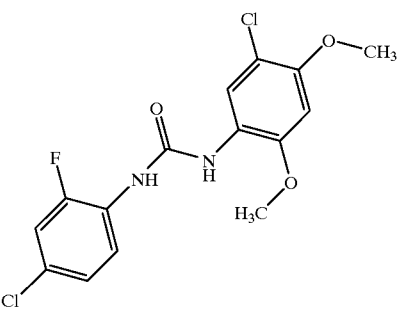 |
| 31 | 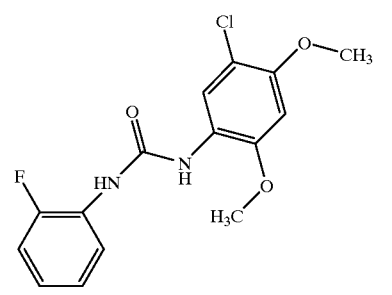 |
| 32 | 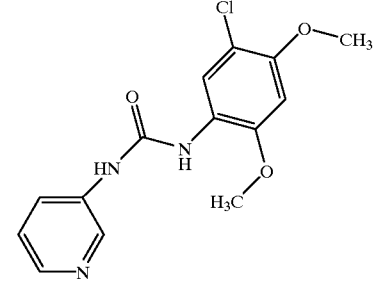 |
| 33 | 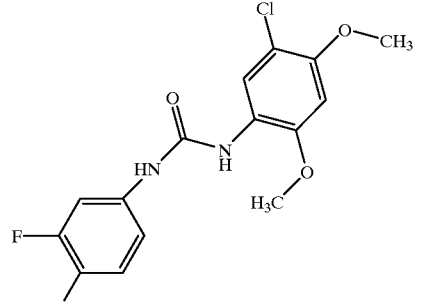 |
| 34 | 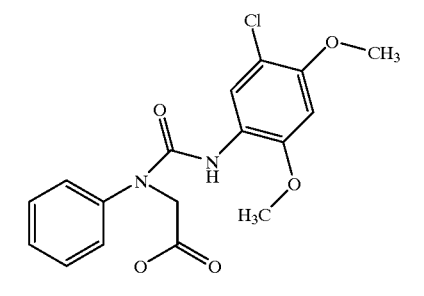 |
| 35 | 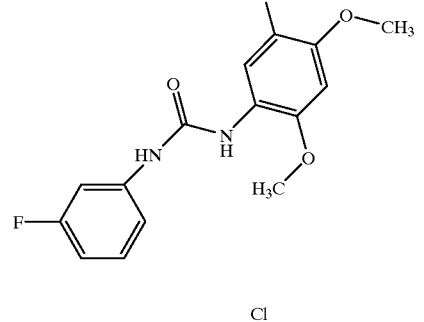 |
| 36 | 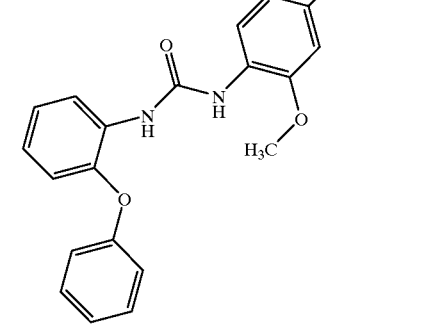 |

TABLE 1-continued

| compound number | Structure |
|---|---|
| 37 | (structure) |
| 38 | (structure) |
| 39 | (structure) |
| 40 | (structure) |
| 41 | (structure) |
| 42 | (structure) |
| 43 | (structure) |
| 44 | (structure) |
| 45 | (structure) |

TABLE 1-continued

| compound number | Structure |
|---|---|
| 46 | (structure) |
| 47 | (structure) |
| 48 | (structure) |
| 49 | (structure) |
| 50 | (structure) |
| 51 | (structure) |
| 52 | (structure) |
| 53 | (structure) |
| 54 | (structure) |
| 55 | (structure) |
| 56 | (structure) |

TABLE 1-continued
| compound number | Structure |
|---|---|
| 57 | 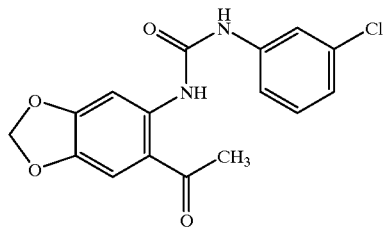 |
| 58 | 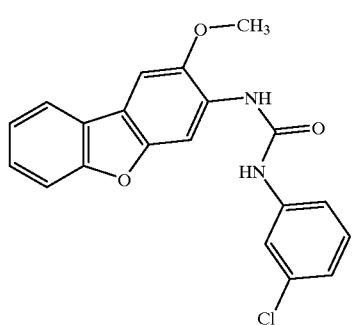 |
| 59 | 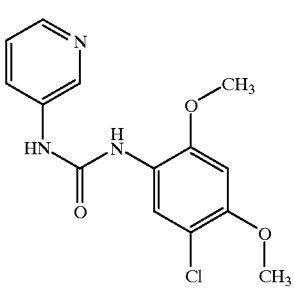 |
| 60 | 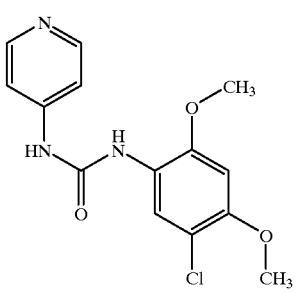 |
| 61 | 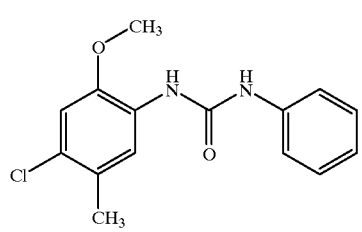 |
| 62 | 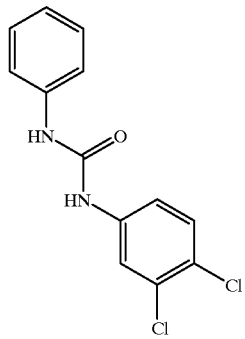 |
| 63 | 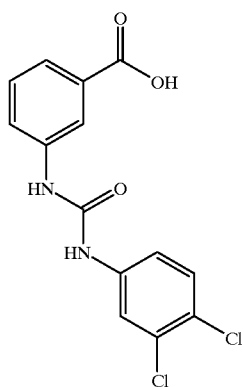 |
| 64 | 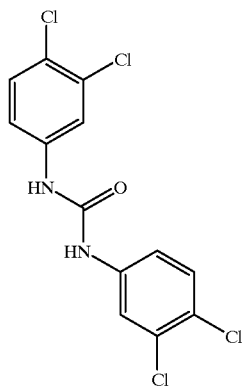 |
| 65 | 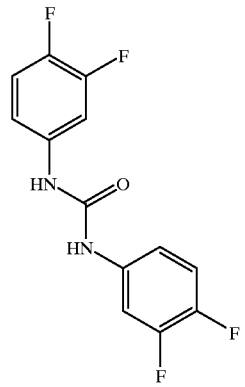 |

TABLE 1-continued

| compound number | Structure |
|---|---|
| 66 | 4-[[[(3,4-dichlorophenyl)amino]carbonyl]amino]-2-methoxybenzoic acid |
| 67 | 4-[[[(3,4-difluorophenyl)amino]carbonyl]amino]-2-methoxybenzoic acid |
| 68 | N-(3,4-dichlorophenyl)-N'-(3,4,5-trimethoxyphenyl)urea |
| 69 | N-(3,4-difluorophenyl)-N'-(3,4,5-trimethoxyphenyl)urea |
| 70 | 3-[[[(3,4-dichlorophenyl)amino]carbonyl]amino]benzamide |
| 71 | 3-[[[(3,4-difluorophenyl)amino]carbonyl]amino]benzamide |

TABLE 1-continued
| compound number | Structure |
|---|---|
| 72 | 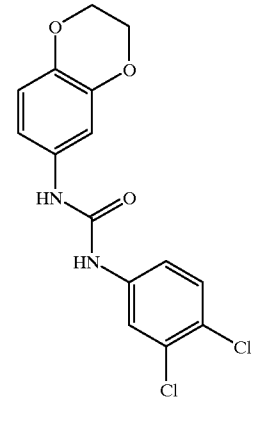 |
| 73 | 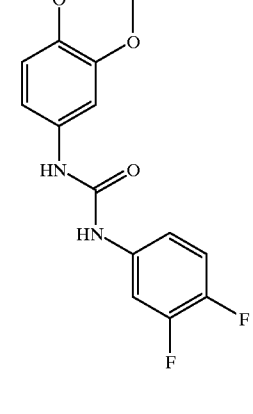 |
| 74 | 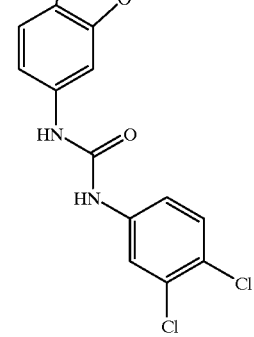 |
| 75 | 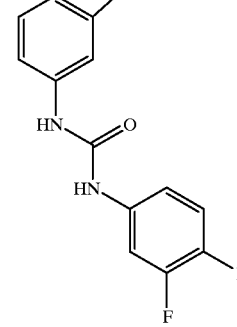 |
| 76 | 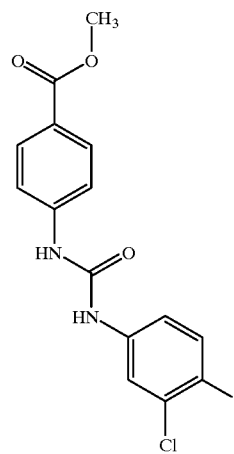 |
| 77 | 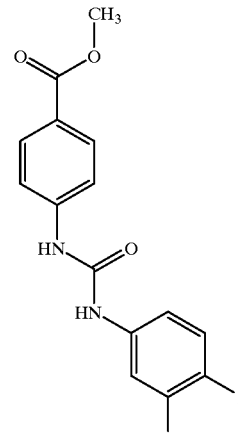 |

TABLE 1-continued

| compound number | Structure |
|---|---|
| 78 | 3,4-dimethoxyphenyl-NH-C(O)-NH-(3,4-dichlorophenyl) |
| 79 | 3,4-dimethoxyphenyl-NH-C(O)-NH-(3,4-difluorophenyl) |
| 80 | 2-methylbenzothiazol-5-yl-NH-C(O)-NH-(3,4-difluorophenyl) |
| 81 | 1H-indazol-5-yl-NH-C(O)-NH-(3,4-dichlorophenyl) |
| 82 | 1H-indazol-5-yl-NH-C(O)-NH-(3,4-difluorophenyl) |
| 83 | 4-methoxyphenyl-NH-C(O)-NH-(3,4-dichlorophenyl) |

TABLE 1-continued
| compound number | Structure |
|---|---|
| 84 | 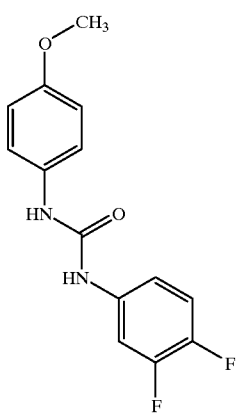 |
| 85 | 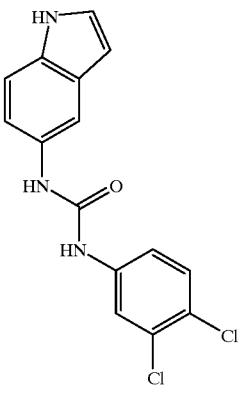 |
| 86 | 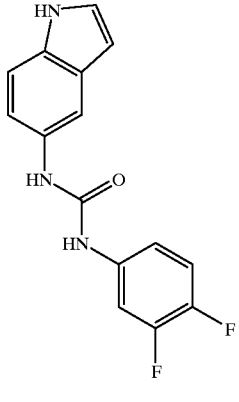 |
| 87 | 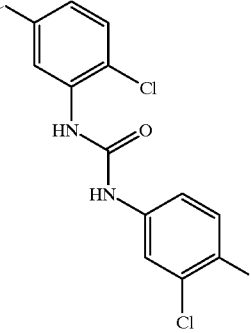 |
| 88 | 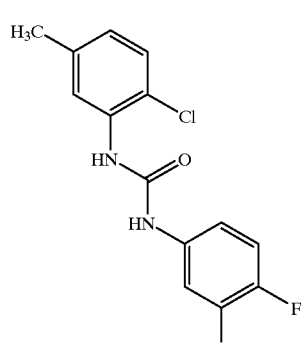 |
| 89 | 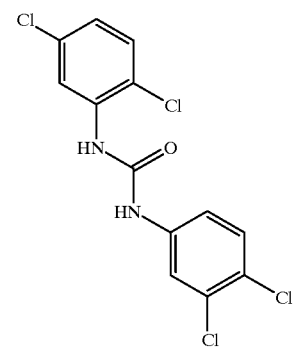 |
| 90 | 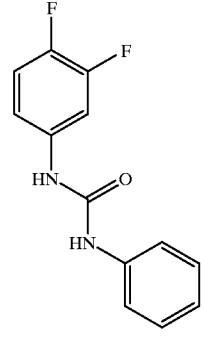 |
| 91 | 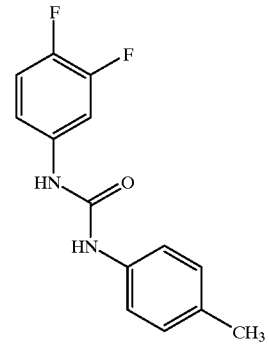 |

TABLE 1-continued

| compound number | Structure |
|---|---|
| 92 | 3,4-difluorophenyl-NH-C(=O)-NH-3,4-dichlorophenyl |
| 93 | 3,4-difluorophenyl-NH-C(=O)-NH-2,4-dichlorophenyl |
| 94 | 3,4-difluorophenyl-NH-C(=O)-NH-3-chlorophenyl |
| 95 | 3,4-difluorophenyl-NH-C(=O)-NH-3,4-difluorophenyl |
| 96 | 3,4-difluorophenyl-NH-C(=O)-NH-(2-chloro-6-methylphenyl) |
| 97 | 3,4-difluorophenyl-NH-C(=O)-NH-C(Cl)=C(CH$_3$)-CH=CH-Cl |
| 98 | 3,4-difluorophenyl-NH-C(=O)-NH-2,6-dichlorophenyl |
| 99 | (3-fluoro-4-methylphenyl)-NH-C(=O)-NH-3,4-dichlorophenyl |

TABLE 1-continued

| compound number | Structure |
|---|---|
| 100 | 1-(3-fluoro-4-methylphenyl)-3-(3,4-difluorophenyl)urea |
| 101 | 1-(6-methoxypyridin-3-yl)-3-(3,4-dichlorophenyl)urea |
| 102 | 1-(6-methoxypyridin-3-yl)-3-(3,4-difluorophenyl)urea |
| 103 | 1-(6-methoxy-4-methylpyridin-3-yl)-3-(3,4-dichlorophenyl)urea |
| 104 | 1-(4-methoxy-2-methylphenyl)-3-(3,4-difluorophenyl)urea |
| 105 | 1-(5-chloro-2,4-dimethoxyphenyl)-3-(3,4-dichlorophenyl)urea |
| 106 | 1-(5-chloro-2,4-dimethoxyphenyl)-3-(3,4-difluorophenyl)urea |

TABLE 1-continued
| compound number | Structure |
|---|---|
| 107 | 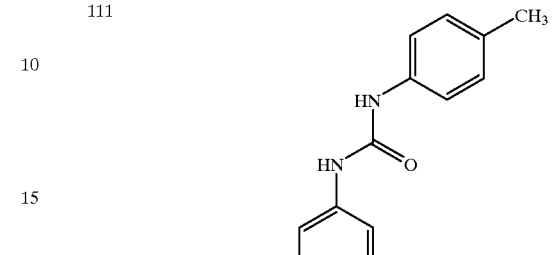 |
| 108 | 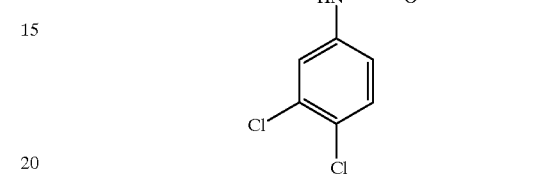 |
| 109 | 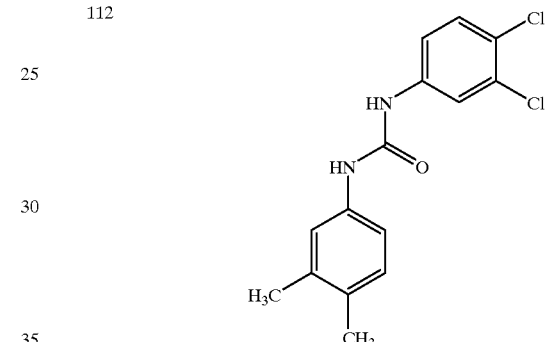 |
| 110 | 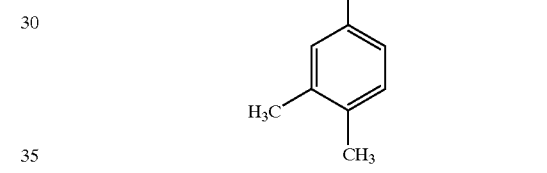 |
TABLE 1-continued
| compound number | Structure |
|---|---|
| 111 | 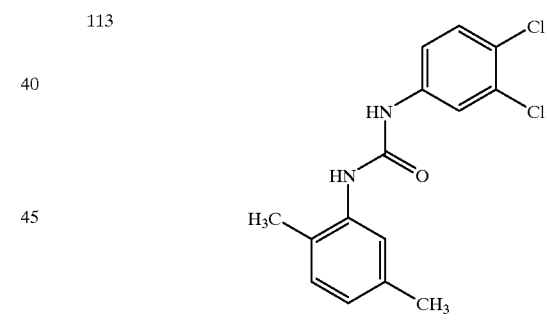 |
| 112 | |
| 113 | 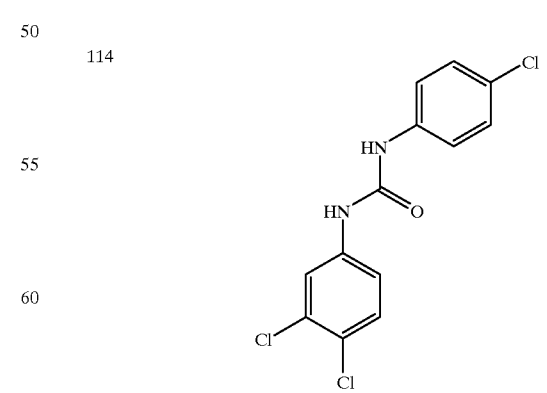 |
| 114 | |

TABLE 1-continued

| compound number | Structure |
|---|---|
| 115 | 4-acetylphenyl-NH-C(O)-NH-(3,4-dichlorophenyl) |
| 116 | 4-(ethoxycarbonyl)phenyl-NH-C(O)-NH-(3,4-dichlorophenyl) |
| 117 | 2-carboxyphenyl-NH-C(O)-NH-(3,4-dichlorophenyl) |
| 118 | (3,4-dichlorophenyl)-NH-C(O)-NH-(3-methoxy-5-methylphenyl) |
| 119 | (3,4-dichlorophenyl)-NH-C(O)-NH-(2-methoxycarbonylphenyl) |
| 120 | (2-fluorophenyl)-NH-C(O)-NH-(3,4-dichlorophenyl) |
| 121 | (2-ethoxyphenyl)-NH-C(O)-NH-(3,4-dichlorophenyl) |

TABLE 1-continued

| compound number | Structure |
|---|---|
| 122 | *(structure)* |
| 123 | *(structure)* |
| 124 | *(structure)* |
| 125 | *(structure)* |
| 126 | *(structure)* |
| 127 | *(structure)* |
| 128 | *(structure)* |
| 129 | *(structure)* |
| 130 | *(structure)* |

TABLE 1-continued

| compound number | Structure |
|---|---|
| 131 | 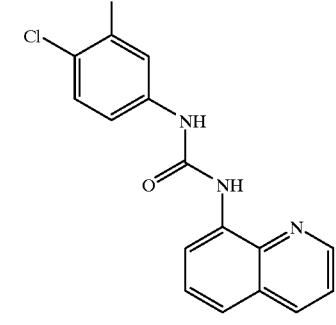 |
| 132 | 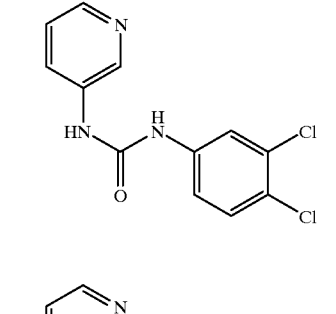 |
| 133 | 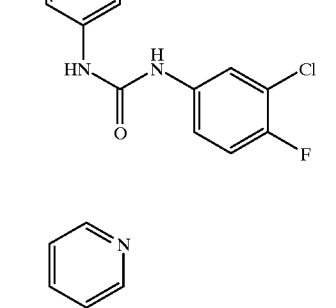 |
| 134 | 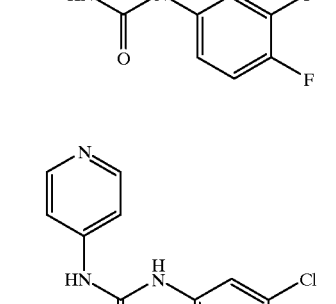 |
| 135 | 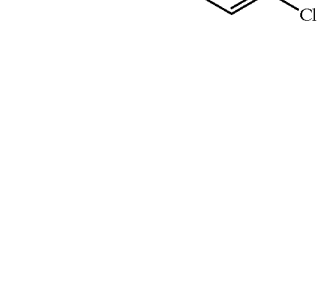 |

TABLE 1-continued

| compound number | Structure |
|---|---|
| 136 | |
| 137 | |
| 138 | |
| 139 | |

Preferred compounds of the present invention are compound numbers 3, 4, 6, 12, 13, 22, 24, 25, 29–31, 33, 35, 61, 64, 105–107, 114, and 120.

More preferred compounds of the present invention are compound numbers 3, 4, 6, 12, 13, 24, 31, 61, 64, 105 and 107.

Compounds of formula (I) may be obtained using conventional synthetic techniques. Preferably, these compounds are chemically synthesized from readily available starting materials. Modular and convergent methods are also preferred. In a convergent approach, for example, large sections of the final product are brought together in the final stages of the synthesis, rather than by incremental addition of small pieces to a growing molecular fragment.

Scheme I illustrates a representative example of a convergent process for the synthesis of compounds of formula (Ia), a subset of compounds of formula (I), wherein Y is oxygen and $X_2$ is NH. The process comprises the reaction of an isocyanate of formula (XI) with an amine, thiol or a hydroxyl compound of formula (X) in a solvent such as methylene chloride. Compounds of formula (I), wherein Y is S or NH can be readily obtained through the process of Scheme 1 by using the thioisocyanate or guanidino analogue of compound of formula (XI), respectively.

Scheme 1

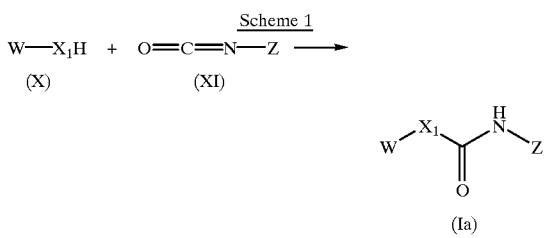

Scheme 2 illustrates a representative example of a convergent process for the synthesis of compounds of formula (Ib), a subset of compounds of formula (I), wherein Y is oxygen. A compound of formula (X) is reacted with a coupling reagent such as phosgene, or a phosgene equivalent such as triphosgene, or diethyl carbonate, followed by reaction with a compound of formula (XII) to yield compound of formula (Ib).

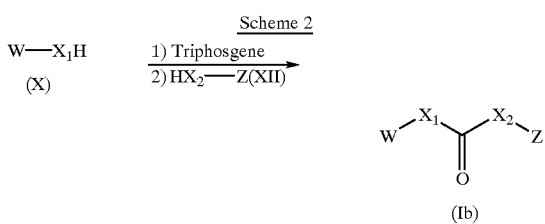

Scheme 3 illustrates a representative example of a convergent process for the synthesis of compounds of formula (Ic), a subset of compounds of formula (I), wherein Y is oxygen and $X_1$ is NH.

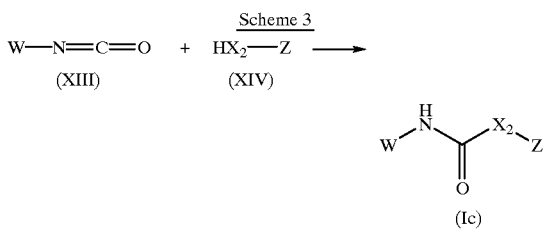

The process of Scheme 3 comprises the reaction of an isocyanate of formula (XIII) with an amine, thiol or a hydroxyl compound of formula (XIV), in a solvent such as methylene chloride, to yield compounds of formula (Ic). Compounds of formula (I), wherein Y is S or NH can be readily obtained through the process of Scheme 3 by using the thioisocyanate or guanidino analogue of compound of formula (XIII), respectively.

The activity of the p38 inhibitors of this invention may be assayed in vitro, in vivo or in a cell line. In vitro assays include assays that determine inhibition of either the kinase activity or ATPase activity of activated p38. Alternate in vitro assays quantitate the ability of the inhibitor to bind to p38 and may be measured either by radiolabelling the inhibitor prior to binding, isolating the inhibitor/p38 complex and determining the amount of radiolabel bound, or by running a competition experiment where new inhibitors are incubated with p38 bound to known radioligands. These and other useful in vitro and cell culture assays are well known to those of skill in the art.

Cell culture assays of the inhibitory effect of the compounds of this invention may be used to determine the amounts of TNF, IL-1, IL-6 or IL-8 produced in whole blood or cell fractions thereof in cells treated with inhibitor as compared to cells treated with negative controls. Level of these cytokines may be determined through the use of commercially available ELISAs.

An in vivo assay useful for determining the inhibitory activity of the p38 inhibitors of this invention are the suppression of hindpaw edema in rats with *Mycobacterium butyricum*-induced adjuvant arthritis. This is described in J. C. Boehm et al., *J. Med. Chem.*, 39, pp. 3929–37 (1996), the disclosure of which is herein incorporated by reference. The p38 inhibitors of this invention may also be assayed in animal models of arthritis, bone resorption, endotocin shock and immune function, as described in A. M. Badger et al.,*J. Pharmacol. Experimental Therapuetics*, 279, pp. 1453–61 (1996), the disclosure of which is herein incorporated by reference.

The p38 inhibitors or pharmaceutical salts thereof may be formulated into pharmaceutical compositions for administration to animals or humans. These pharmaceutical compositions, which comprise an amount of p38 inhibitor effective to treat or prevent a p38-mediated condition and a pharmaceutically acceptable carrier, are another embodiment of the present invention. The term "p38-mediated condition" as used herein means any disease or other deleterious condition in which p38 is known to play a role. This includes conditions which are known to be caused by IL-1, TNF, IL-6 or IL-8 overproduction. Such conditions include, without limitation, inflammatory diseases, autoimmune diseases, destructive bone disorders, proliferative disorders, infectious diseases, viral disease, and neurodegenerative diseases.

Inflammatory diseases which may be treated or prevented include, but are not limited to, acute pancreatitis, chronic pancreatitis, asthma, allergies, and adult respiratory distress syndrome.

Autoimmune diseases which may be treated or prevented include, but are not limited to, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

Destructive bone disorders which may be treated or prevented include, but are not limited to, osteoporosis, osteoarthritis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Infectious diseases which may be treated or prevented include, but are not limited to, sepsis, septic shock, and Shigellosis.

Viral diseases which may be treated or prevented include, but are not limited to, acute hepatitis infection (including hepatitis A, hepatitis B and hepatitis C), HIV infection and CMV retinitis.

Degenerative conditions or diseases which may be treated or prevented by the compounds of this invention include, but are not limited to, Alzheimer's disease, Parkinson's disease, cerebral ischemia and other neurodegenerative diseases.

"p38-mediated conditions" also include ischemia/reperfusion in stroke, heart attacks, myocardial ischemia, organ hypoxia, vascular hyperplasia, cardiac hypertrophy and thrombin-induced platelet aggregation.

In addition, p38 inhibitors of this invention are also capable of inhibiting the expression of inducible pro-inflammatory proteins such as prostaglandin endoperoxide synthase-2 (PGHS-2), also referred to as cyclooxygenase-2 (COX-2). Therefore, other "p38-mediated conditions" are edema, analgesia, fever and pain, such as neuromuscular pain, headache, cancer pain, dental pain and arthritis pain.

The conditions and diseases that may be treated or prevented by the p38 inhibitors of this invention may also be conveniently grouped by the cytokine (e.g., IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscel degeneration, cachexia, psoriatic arthritis, Reiter's syndrome, gout, traumatic arthritis, rubella arthritis, acute synovitis, diabetes, pancreatic β-cell disease and Alzheimer's disease.

A TNF-mediated disease or condition includes rheumatoid arthritis, rheumatoid spndylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and vetinary viral infections, such as lentivirus infections, including, but not limited to equine infectious anaemia virus, caprine arthritis virus, visna virus or maedi virus; or retrovirus infections, including feline immunodeficiency virus, bovine immunodeficiency virus, or canine immunodeficiency virus.

IL-8 mediated disease or conditon includes diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this infection may be used topically to treat or prevent conditions caused or exacerbated by IL-1 or TNF. Such conditions include inflamed joints, eczema, psoriasis, inflammatory skin conditions such as sunburn, inflammatory eye conditions such as conjuctivitis, pyresis, pain and other conditions associated with inflammation.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethyl-cellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including conditions and diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of p38 inhibitor that may be combined with the carrier materials to produce a single dosage form will vary depending upon the host treated the particular mode of administration. Preferably, the compositions should be formulated so that a dosage of between 0.01–100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a p38-mediated condition comprising the step of administering to a patient one of the above-described pharmaceutical compositions. The term "patient", as used herein, means an animal, preferably a human.

Preferably, that method is used to treat or prevent a condition selected from inflammatory diseases, autoimmune diseases, destructive bone disorders, proliferative disorders, infectious diseases, degenerative diseases, allergies, reperfusion/ischemia in stroke, heart attacks, organ hypoxia, vascular hyperplasia, cardiac hypertrophy, and thrombin-induced platelet aggregation.

According to another embodiment, the inhibitors of this invention are used to treat or prevent an IL-1, IL-6, IL-8 or TNF-mediated disease or condition. Such conditions are described above.

Depending upon the particular p38-mediated condition to be treated or prevented, additional drugs, which are normally administered to treat or prevent that condition may be administered together with the inhibitors of this invention. Those additional agents may be administered separately, as part of a multiple dosage regimen, from the p38 inhibitor-containing composition. Alternatively, those agents may be part of a single dosage form, mixed together with the p38 inhibitor in a single composition.

All references cited are herein incorporated by reference.

In order that the invention described herein may be more fully understood, the following examples are set forth. It should be understood that these examples are for illustrative purposes only and are not to be construed as limiting this invention in any manner.

EXAMPLE 1

Synthesis of p38 Inhibitor Compound 138

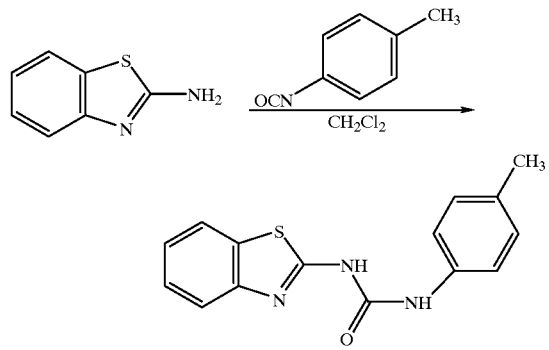

2-amino benzothiazole (500 mg, 2.77 mmol) and 4-methylphenylisocyanate (301 uL, 2.77 mmol) were stirred together at room temperature using methylene chloride as a solvent (50 mL). The product from this reaction precipitated from the solvent mixture and was filtered and washed with methylene chloride to yield pure product: 232 mg, 30% yield. TLC Rf=0.55 eluting with 10% methanol in methylene chloride.

EXAMPLE 2

Synthesis of p38 Inhibitor Compound 139

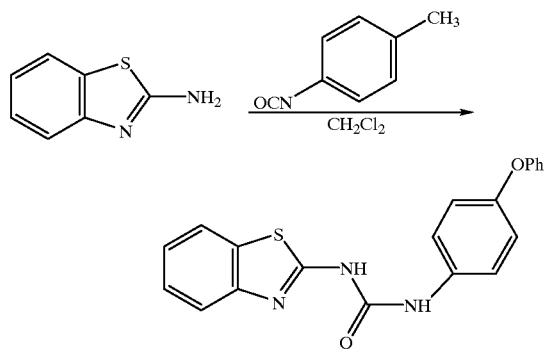

The same procedure as Example 1 was followed using 4-phenoxyphenylisocyanate. The same scale was used. Pure product was obtained 0.896 mg, 89% yield, Rf=0.31 eluting with 10% methanol in methylene chloride.

EXAMPLE 3

Synthesis of p38 Inhibitor Compound 4

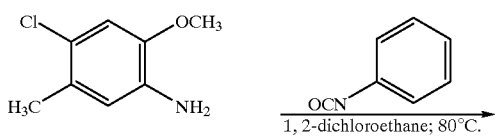

-continued

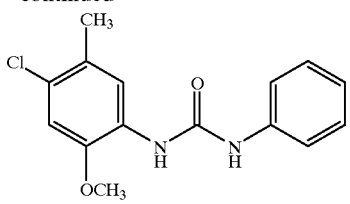

4-chloro-2-methoxy-5-methylaniline (34.3 mg, 0.2 mmol) and a 1M solution of phenylisocyanate in 1,2 dichloroethane (270 ul, 0.27 mmol) were stirred together at 80° C. in 1,2 dichloroethane (1 mL). The reaction was heated overnight, then cooled and passed through a Varian Bond-Elut SCX cation exchange resin. The filtrate was evaporated in vacuo to yield pure product.

EXAMPLE 4
Synthesis of p38 Inhibitor Compound 6

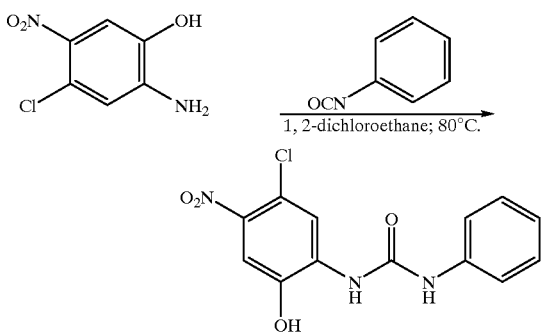

2-amino-4-chloro-5-nitrophenol (41.4 mg, 0.22 mmol) and a 1M solution of phenylisocyanate in 1,2 dichloroethane (270 ul, 0.27 mmol) were stirred together at 80° C. in 1,2 dichloroethane (1 mL). The reaction was heated overnight, then cooled and passed through a Varian Bond-Elut SCX cation exchange resin. The filtrate was evaporated in vacuo to yield pure product.

EXAMPLE 5
Synthesis of p38 Inhibitor Compound 13

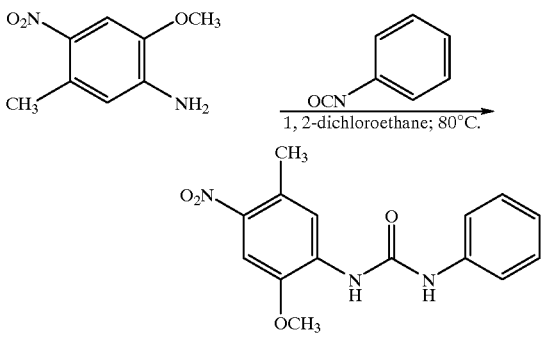

3-methyl-4-nitro-o-anisidine (37.8 mg, 0.207 mmol) and a 1M solution of phenylisocyanate in 1,2 dichloroethane (270 ul, 0.27 mmol) were stirred together at 80° C. in 1,2 dichloroethane (1 mL). The reaction was heated overnight, then cooled and passed through a Varian Bond-Elut SCX cation exchange resin. The filtrate was evaporated in vacuo to yield pure product.

EXAMPLE 6
Synthesis of p38 Inhibitor Compound 13

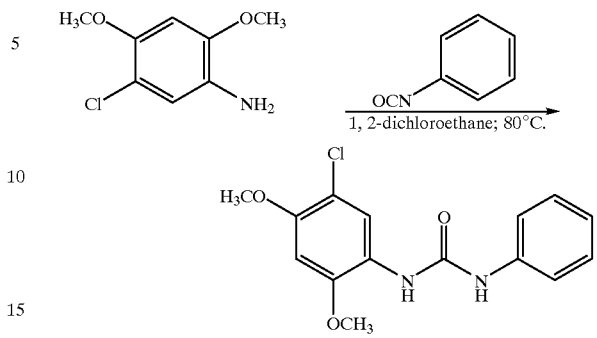

5-chloro-2,4-dimethoxyaniline (39,1 mg, 0.208 mmol) and a 1M solution of phenylisocyanate in 1,2 dichloroethane (270 ul, 0.27 mmol) were stirred together at 80° C. in 1,2 dichloroethane (1 mL). The reaction was heated overnight, then cooled. Product precipitated from the reaction and was filtered and washed with dichloroethane to yield pure product.

EXAMPLE 7
Cloning of p38 Kinase in Insect Cells

Two splice variants of human p38 kinase, CSBP1 and CSBP2, have been identified. Specific oligonucleotide primers were used to amplify the coding region of CSBP2 cDNA using a HeLa cell library (Stratagene) as a template. The polymerase chain reaction product was cloned into the pET-15b vector (Novagen). The baculovirus transfer vector, pVL-(His)6-p38 was constructed by subcloning a XbaI-BamHI fragment of pET15b-(His)6-p38 into the complementary sites in plasmid pVL1392 (Pharmingen).

The plasmid pVL-(His)6-p38 directed the synthesis of a recombinant protein consisting of a 23-residue peptide (MGSSHHHHHHSSGLVPRGSHMLE, where LVPRGS represents a thrombin cleavage site) fused in frame to the N-terminus of p38, as confirmed by DNA sequencing and by N-terminal sequencing of the expressed protein. Monolayer culture of *Spodoptera frugiperda* (Sf9) insect cells (ATCC) was maintained in TNM-FH medium (Gibco BRL) supplemented with 10% fetal bovine serum in a T-flask at 27° C. Sf9 cells in log phase were co-transfected with linear viral DNA of *Autographa califonica* nuclear polyhedrosis virus (Pharmingen) and transfer vector pVL-(His)6-p38 using Lipofectin (Invitrogen). The individual recombinant baculovirus clones were purified by plaque assay using 1% low melting agarose.

EXAMPLE 8
Expression And Purification of Recombinant p38 Kinase

*Trichoplusia ni* (Tn-368) High-Five™ cells (Invitrogen) were grown in suspension in Excel-405 protein free medium (JRH Bioscience) in a shaker flask at 27° C. Cells at a density of $1.5 \times 10^6$ cells/ml were infected with the recombinant baculovirus described above at a multiplicity of infection of 5. The expression level of recombinant p38 was monitored by immunoblotting using a rabbit anti-p38 antibody (Santa Cruz Biotechnology). The cell mass was harvested 72 hours after infection when the expression level of p38 reached its maximum.

Frozen cell paste from cells expressing the $(His)_6$-tagged p38 was thawed in 5 volumes of Buffer A (50 mM NaH2PO4 pH 8.0, 200 mM NaCl, 2 mM β-Mercaptoethanol, 10%

Glycerol and 0.2 mM PMSF). After mechanical disruption of the cells in a Microfluidizer, the lysate was centrifuged at 30,000×g for 30 minutes. The supernatant was incubated batchwise for 3–5 hours at 4° C. with Talonm (Clontech) metal affinity resin at a ratio of 1 ml of resin per 2–4 mgs of expected p38. The resin was settled by centrifugation at 500×g for 5 minutes and gently washed batchwise with Buffer A. The resin was slurried and poured into a column (approx. 2.6×5.0 cm) and washed with Buffer A+5 mM imidizole.

The $(His)_6$-p38 was eluted with Buffer A+100 mM imidizole and subsequently dialyzed overnight at 4° C. against 2 liters of Buffer B, (50 mM HEPES, pH 7.5, 25 mM β-glycerophosphate, 5% glycerol, 2 mM DTT). The $His_6$ tag was removed by addition of at 1.5 units thrombin (Calbiochem) per mg of p38 and incubation at 20° C. for 2–3 hours. The thrombin was quenched by addition of 0.2 mM PMSF and then the entire sample was loaded onto a 2 ml benzamidine agarose (American International Chemical) column.

The flow through fraction was directly loaded onto a 2.6×5.0 cm Q-Sepharose (Pharmacia) column previously equilibrated in Buffer B+0.2 mM PMSF. The p38 was eluted with a 20 column volume linear gradient to 0.6M NaCl in Buffer B. The eluted protein peak was pooled and dialyzed overnight at 4° C. vs. Buffer C (50 mM HEPES pH 7.5, 5% glycerol, 50 mM NaCl, 2 mM DTT, 0.2 mM PMSF).

The dialyzed protein was concentrated in a Centriprep (Amicon) to 3–4 mls and applied to a 2.6×100 cm Sephacryl S-100HR (Pharmacia) column. The protein was eluted at a flow rate of 35 mls/hr. The main peak was pooled, adjusted to 20 mM DTT, concentrated to 10–80 mgs/ml and frozen in aliquots at −70° C. or used immediately.

EXAMPLE 9

Activation of p38

P38 was activated by combining 0.5 mg/ml p38 with 0.005 mg/ml DD-double mutant MKK6 in Buffer B+10 mM MgCl2, 2 mM ATP, 0.2 mM Na2VO4 for 30 minutes at 20° C. The activation mixture was then loaded onto a 1.0×10 cm MonoQ column (Pharmacia) and eluted with a linear 20 column volume gradient to 1.0 M NaCl in Buffer B. The activated p38 eluted after the ADP and ATP. The activated p38 peak was pooled and dialyzed against buffer B+0.2 mM Na2VO4 to remove the NaCl. The dialyzed protein was adjusted to 1.1M potassium phosphate by addition of a 4.0M stock solution and loaded onto a 1.0×10 cm HIC (Rainin Hydropore) column previously equilibrated in Buffer D (10% glycerol, 20 mM β-glycerophosphate, 2.0 mM DTT)+ 1.1MK2HPO4. The protein was eluted with a 20 column volume linear gradient to Buffer D+50 mM K2HPO4. The double phosphorylated p38 eluted as the main peak and was pooled for dialysis against Buffer B+0.2 mM Na2VO4. The activated p38 was stored at −70° C.

EXAMPLE 10 p38 Inhibition Assays

Inhibition of Phosphorylation of EGF Receptor Peptide

This assay was carried out in the presence of 10 mM MgCl2, 25 mM β-glycerophosphate, 10% glycerol and 100 mM HEPES buffer at pH 7.6. For a typical IC50 determination, a stock solution was prepared containing all of the above components and activated p38 (5 nM). The stock solution was aliquotted into vials. A fixed volume of DMSO or inhibitor in DMSO (final concentration of DMSO in reaction was 5%) was introduced to each vial, mixed and incubated for 15 minutes at room temperature. EGF receptor peptide, KRELVEPLTPSGEAPNQALLR, a phosphoryl acceptor in p38-catalyzed kinase reaction (1), was added to each vial to a final concentration of 200 μM. The kinase reaction was initiated with ATP (100 μM) and the vials were incubated at 30° C. After 30 minutes, the reactions were quenched with equal volume of 10% trifluoroacetic acid (TFA).

The phosphorylated peptide was quantified by HPLC analysis. Separation of phosphorylated peptide from the unphosphorylated peptide was achieved on a reverse phase column (Deltapak, 5 μm, C18 100D, part no. 011795) with a binary gradient of water and acetonitrile, each containing 0.1% TFA. IC50 (concentration of inhibitor yielding 50% inhibition) was determined by plotting the % activity remaining against inhibitor concentration.

The results for several of the inhibitors of this invention are depicted in Table 2 below:

TABLE 2

| Compound | $IC_{50}$ (μM) |
| --- | --- |
| 3 | 0.37 |
| 4 | 0.1 |
| 6 | 0.14 |
| 10 | 4.2 |
| 12 | 0.38 |
| 13 | 0.14 |
| 15 | 5.8 |
| 20 | 8 |
| 22 | 1.9 |
| 24 | 0.5 |
| 25 | 1.0 |
| 28 | 7.4 |
| 29 | 1.45 |
| 30 | 1.2 |
| 31 | 0.5 |
| 33 | 1.82 |
| 34 | 19 |
| 35 | 0.63 |
| 35 | 0.63 |
| 37 | 5.1 |
| 40 | 1.5 |
| 61 | 0.14 |
| 62 | 5.6 |
| 63 | 5.8 |
| 64 | 0.13 |
| 105 | 0.5 |
| 106 | 1.82 |
| 107 | 0.1 |
| 118 | 14.7 |
| 119 | 6.3 |
| 121 | 2.2 |
| 122 | 15.1 |
| 125 | 8.4 |
| 126 | 5.6 |
| 131 | 6.3 |

Other inhibitors of this invention will also inhibit the kinase activity of p38.

while we have hereinbefore presented a number of embodiments of this invention, it is apparent that our basic construction can be altered to provide other imbodiments which utilize the methods of this invention.

We claim:

1. A compound of the formula:

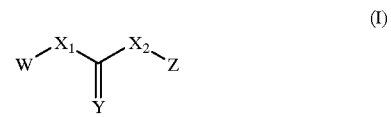

(I)

wherein:

W is an aromatic monocyclic, bicyclic or tricyclic ring system wherein W optionally comprises up to 4 substituents independently selected from $R^1$ and $R^4$;

wherein $R^1$ is halogen, OH, $OR^3$, $NO_2$, $NH_2$, $N(R^3)_2$, $CO_2H$, $CO_2R^3$, $CONH_2$, $CON(R^3)_2$, COH, $COR^3$, NHCOH, $NHCOR^3$, $SO_2NH$, $SO_2NR^3$, CN, SH, $SR^3$, 1,2-methyleneoxy, 1,2-ethylenedioxy, phenyl or $CF_3$;

Y is O or NH;

$X_1$ and $X_2$ are $NR^2$;

wherein $R^2$ is selected from H or $C_1$–$C_6$ straight or branched alkyl, $C_2$–$C_6$ straight or branched alkenyl or alkynyl, wherein $R^2$ is optionally substituted with —OH, —$N(R^3)_2$, —Z, —$CO_2H$, —$CO_2R^3$ or —CO—$N(R^3)_2$;

$R^3$ is selected from phenyl, $C_1$–$C_6$ straight or branched alkyl, $C_2$–$C_6$ straight or branched alkenyl or alkynyl, wherein $R^3$ is optionally substituted with halo, —OH, —$OR^4$, —$NO_2$, —$NH_2$, —$N(R^4)_2$, —$CO_2R^4$, —CO—$N(R^4)_2$, —Z, —CN, —$SR^4$, $CF_3$ or —$SO_2NR^4$;

provided that when Y is O and $R^2$ is H, then $R^3$ is not substituted with OH or $NH_2$ and $R^1$ is not OH, $CO_2H$, COH, NHCOH, SH or $SO_2NH$;

$R^4$ is independently ($C_1$–$C_6$)-straight or branched alkyl, ($C_2$–$C_6$)-straight or branched alkenyl or alkynyl;

Z is selected from a monocyclic, bicyclic or tricyclic aromatic ring system comprising 5–7 members per ring, and wherein Z optionally comprises up to 4 substituents independently selected from $R^1$ and $R^4$;

provided that when Y is O and $R^2$ is H, then W and Z are not both simultaneously substituted or unsubstituted aromatic monocyclic or bicyclic ring systems comprising up to 3 substituents.

2. The compound according to claim 1, wherein W is an aromatic 5–7 membered monocyclic or bicylic ring system wherein W comprises up to 4 substituents selected from $R^1$ or $R^4$.

3. The compound according to claim 2, wherein W is an aromatic 6 membered monocyclic ring and wherein W comprises up to 4 substituents selected from $R^1$ or $R^4$.

4. The compound according to claim 1, wherein W is a phenyl ring optionally comprising up to 3 substituents selected from halo, methyl, methoxy, ethoxy, 1,2-methyleneoxy, 1,2-ethylenedioxy, —COOH, —$COOCH_3$, or —$COOC_2H_5$.

5. The compound according to claim 1, wherein Z is a monocyclic or bicyclic, aromatic ring system comprising 5–7 members per ring, and wherein Z optionally comprises up to 4 substituents independently selected from halo, $OR^3$, $NO_2$, $NH_2$, $N(R^3)_2$, $CO^2R^3$, $CON(R^3)_2$, $COR^3$, $NHCOR^3$, $SO_2NR^3$, CN, $SR^3$, 1,2-methyleneoxy, 1,2-ethylenedioxy, $CF_3$, ($C_1$–$C_6$)-straight or branched alkyl, ($C_2$–$C_6$)-straight or branched alkenyl or alkynyl.

6. The compound according to claim 5, wherein Z is phenyl and comprises up to 3 substituents selected from halo, $OR^3$, $NO_2$, $NH_2$, $N(R^3)_2$, $CO_2R^3$, $CON(R^3)_2$, $COR^3$, $NHCOR^3$, $SO_2NR^3$, CN, $SR^3$, 1,2-methyleneoxy, 1,2-ethylenedioxy, $CF_3$, or ($C_1$–$C_6$)-straight or branched alkyl.

7. The compound according to claim 6, wherein Z is 2,4,5-trisubstituted phenyl or 3,4-disubstituted phenyl, wherein the substituents are selected from halo, $OR^3$, $NO_2$, $NH_2$, $N(R^3)_2$, $CO_2R^3$, $CON(R^3)_2$, $COR^3$, $NHCOR^3$, $SO_2NR^3$, CN, $SR^3$, 1,2-methyleneoxy, 1,2-ethylenedioxy, $CF_3$ or ($C_1$–$C_6$)-straight or branched alkyl.

8. A compound selected from the following:

| compound number | Structure |
|---|---|
| 1 | *(structure: N-phenyl-N'-(2,4,5-trichlorophenyl)urea)* |
| 2 | *(structure: N-phenyl-N'-(4,5-dimethyl-2-nitrosophenyl)urea)* |
| 3 | *(structure: N-phenyl-N'-(4-chloro-2-methyl-5-nitrophenyl)urea)* |
| 4 | *(structure: N-phenyl-N'-(4-chloro-2-methoxy-5-methylphenyl)urea)* |
| 5 | *(structure: N-phenyl-N'-(2-methyl-4-hydroxy-5-methylphenyl)urea)* |
| 6 | *(structure: N-phenyl-N'-(5-chloro-4-nitro-2-hydroxyphenyl)urea)* |

-continued
| compound number | Structure |
|---|---|
| 7 | 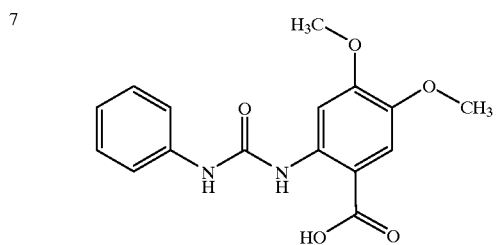 |
| 8 | 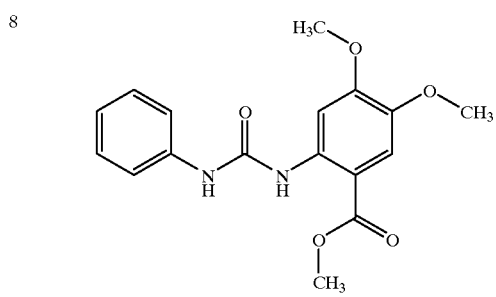 |
| 9 | 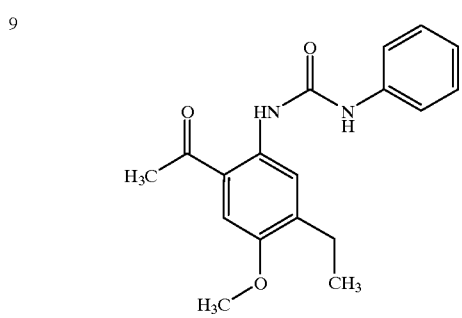 |
| 10 | 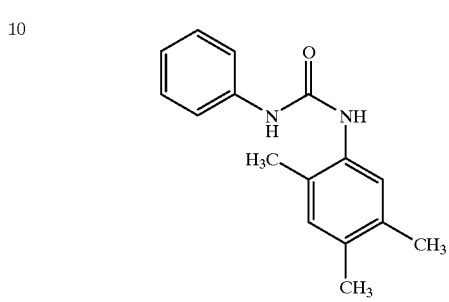 |
| 11 | 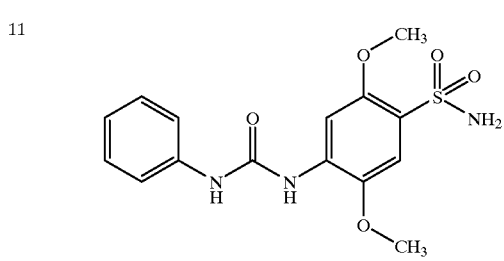 |
-continued
| compound number | Structure |
|---|---|
| 12 | 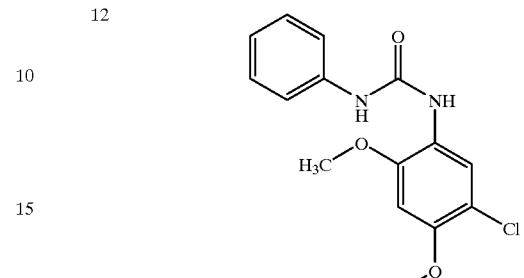 |
| 13 | 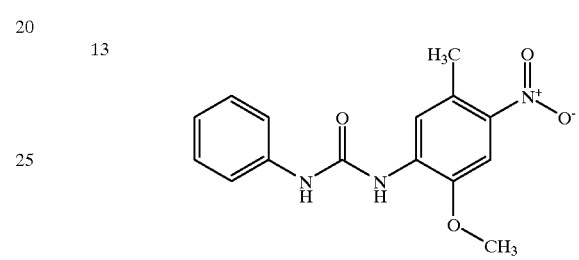 |
| 14 | 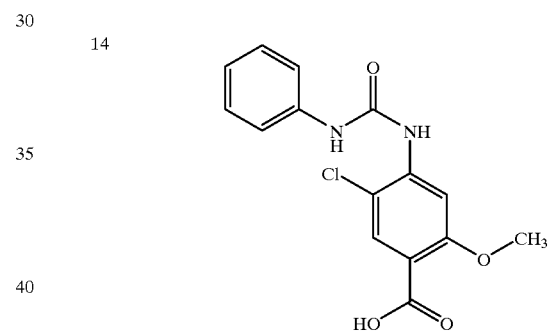 |
| 15 | 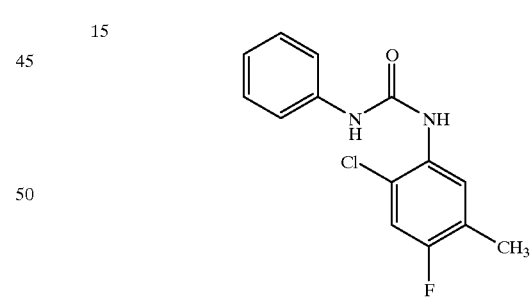 |
| 17 | 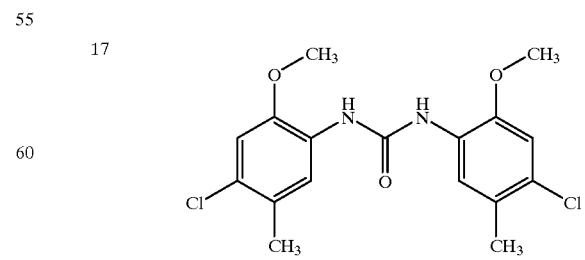 |

-continued
| compound number | Structure |
|---|---|
| 19 | 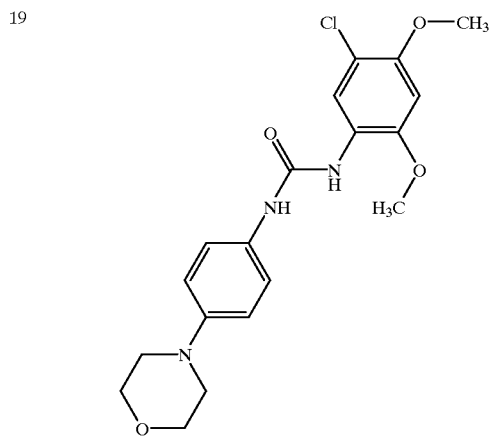 |
| 20 | 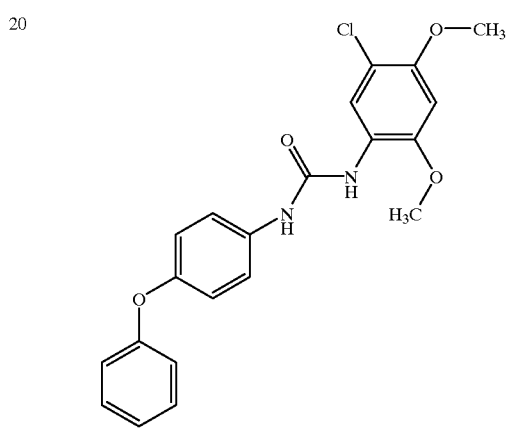 |
| 21 | 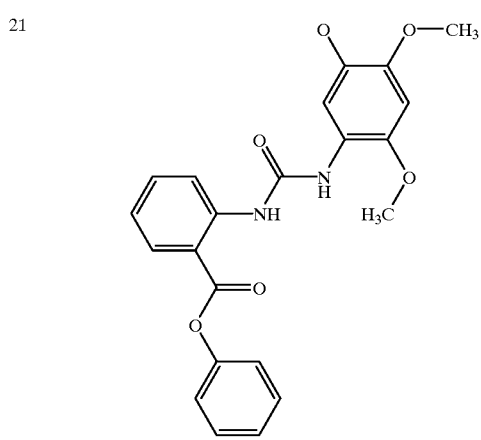 |
-continued
| compound number | Structure |
|---|---|
| 22 | 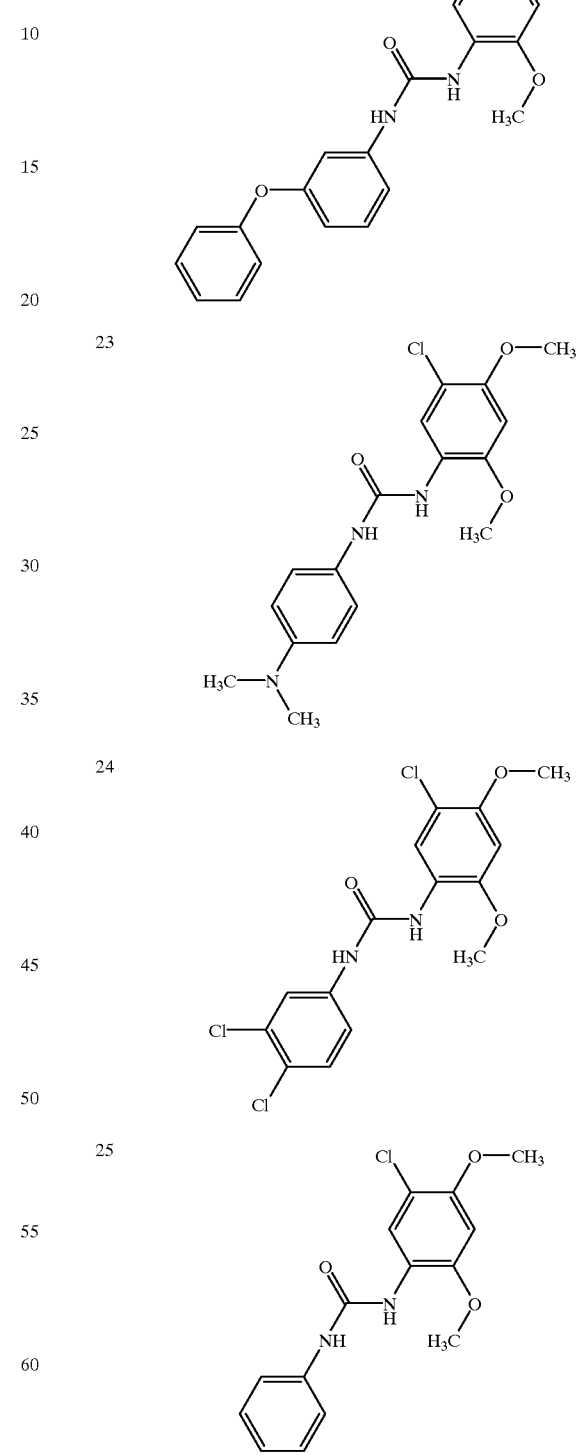 |
| 23 | |
| 24 | |
| 25 | |

-continued
| compound number | Structure |
|---|---|
| 27 | 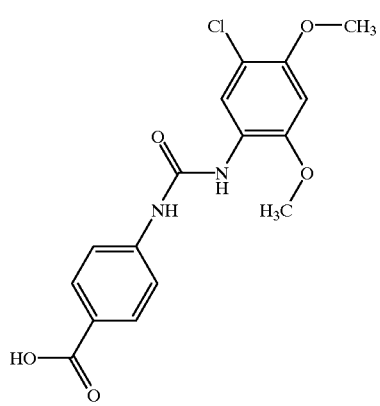 |
| 28 | 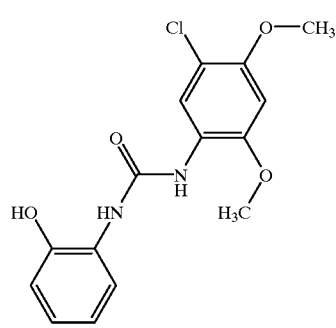 |
| 29 | 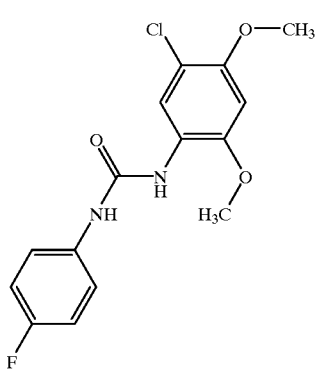 |
| 30 | 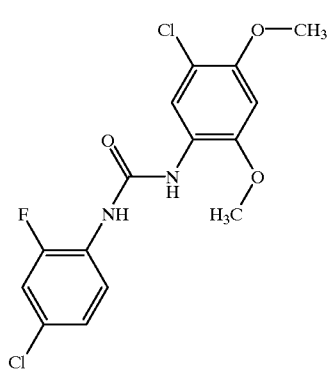 |
-continued
| compound number | Structure |
|---|---|
| 31 | 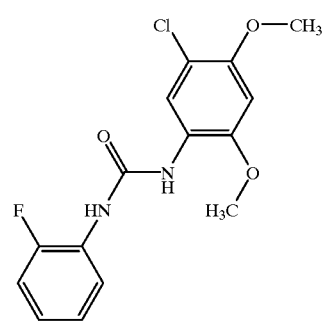 |
| 33 | 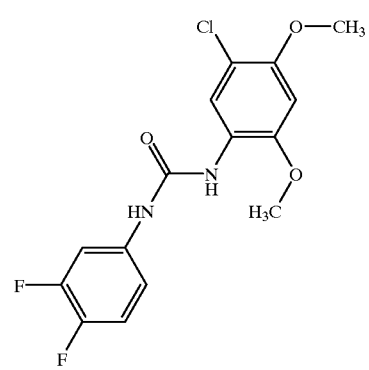 |
| 34 | 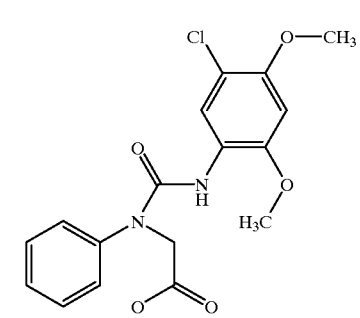 |
| 35 | 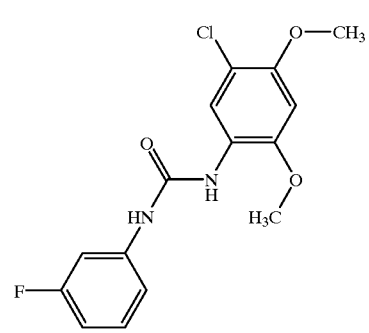 |

-continued
| compound number | Structure |
|---|---|
| 36 | 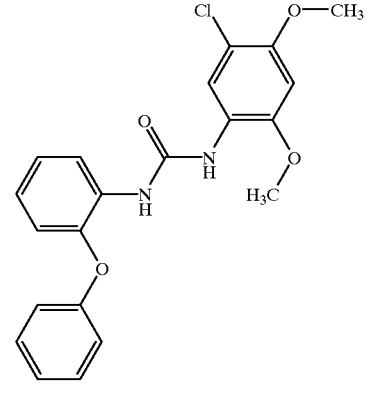 |
| 37 | |
| 38 | |
-continued
| compound number | Structure |
|---|---|
| 39 | 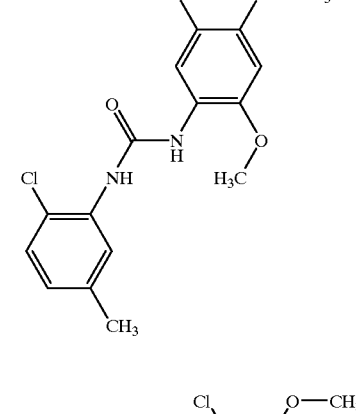 |
| 41 | |
| 44 | 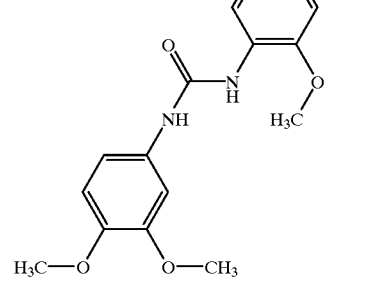 |
| 45 | |
| 46 | |

-continued
| compound number | Structure |
|---|---|
| 47 | 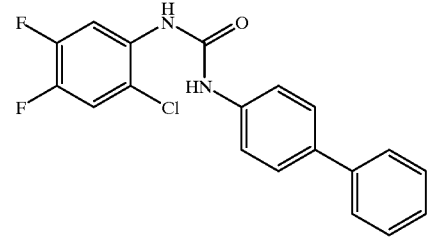 |
| 52 | |
| 53 | |
| 54 | |
-continued
| compound number | Structure |
|---|---|
| 55 | 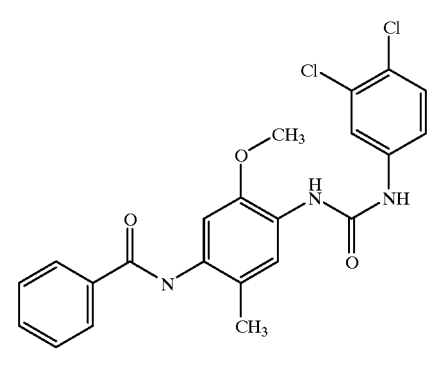 |
| 61 | |
| 62 | |
| 63 | |

-continued
| compound number | Structure |
|---|---|
| 64 | 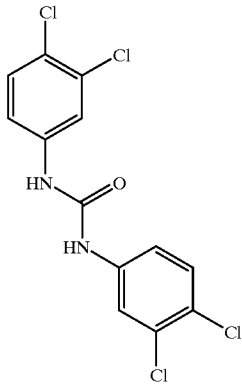 |
| 65 | 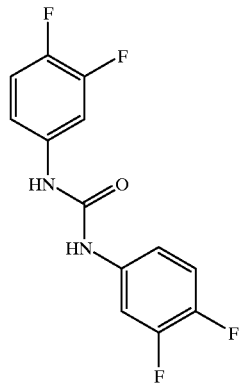 |
| 66 | 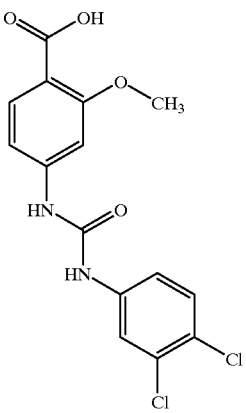 |
-continued
| compound number | Structure |
|---|---|
| 67 | 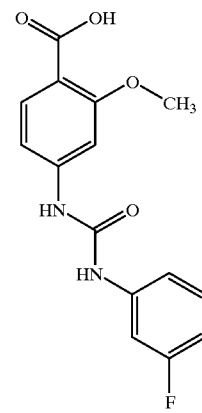 |
| 68 | 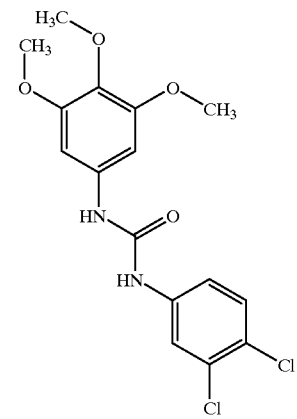 |
| 69 | 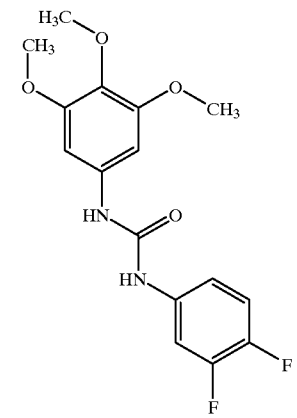 |

-continued
| compound number | Structure |
|---|---|
| 70 | 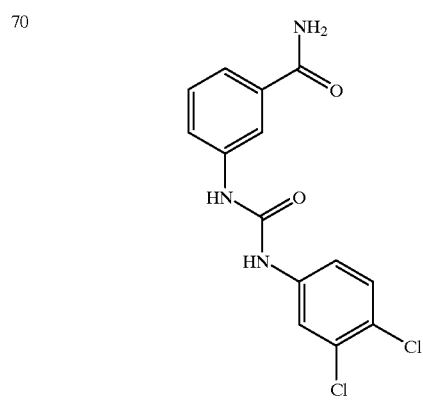 |
| 71 | 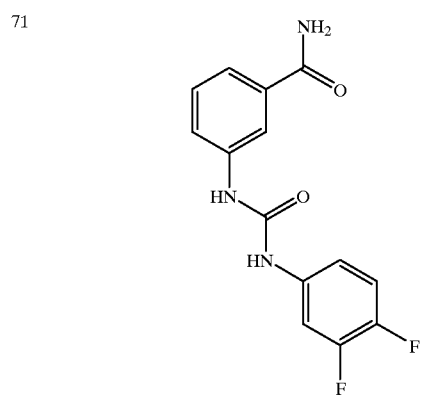 |
| 76 | 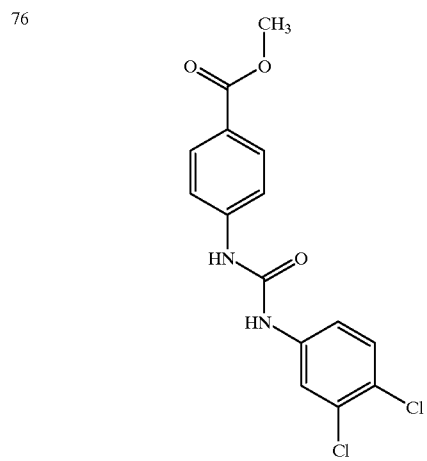 |
-continued
| compound number | Structure |
|---|---|
| 77 | 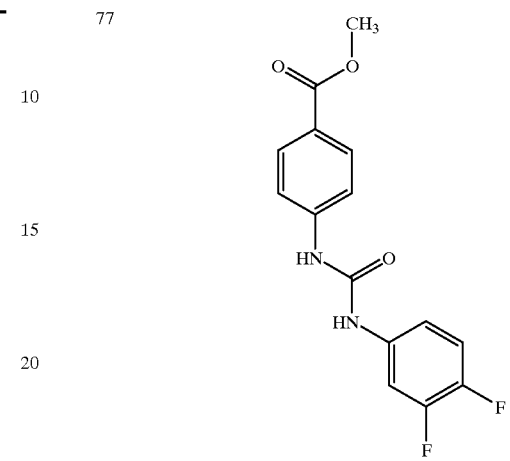 |
| 78 | 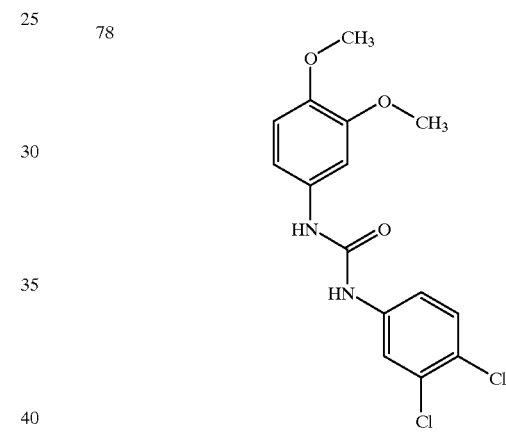 |
| 79 | 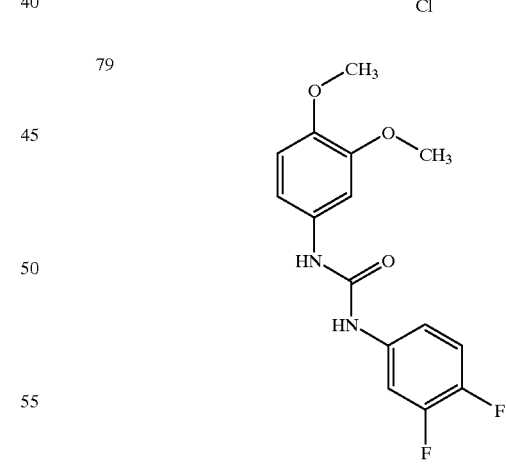 |

-continued

| compound number | Structure |
|---|---|
| 83 | 4-methoxyphenyl-NH-C(=O)-NH-(3,4-dichlorophenyl) |
| 84 | 4-methoxyphenyl-NH-C(=O)-NH-(3,4-difluorophenyl) |
| 87 | (2-chloro-5-methylphenyl)-NH-C(=O)-NH-(3,4-dichlorophenyl) |
| 88 | (2-chloro-5-methylphenyl)-NH-C(=O)-NH-(3,4-difluorophenyl) |

-continued

| compound number | Stucture |
|---|---|
| 89 | (2,5-dichlorophenyl)-NH-C(=O)-NH-(3,4-dichlorophenyl) |
| 90 | (3,4-difluorophenyl)-NH-C(=O)-NH-phenyl |
| 91 | (3,4-difluorophenyl)-NH-C(=O)-NH-(4-methylphenyl) |
| 92 | (3,4-difluorophenyl)-NH-C(=O)-NH-(3,4-dichlorophenyl) |

-continued
| compound number | Structure |
|---|---|
| 93 | 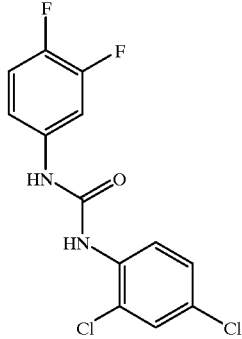 |
| 94 | 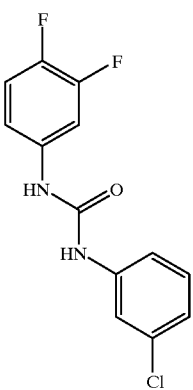 |
| 95 | 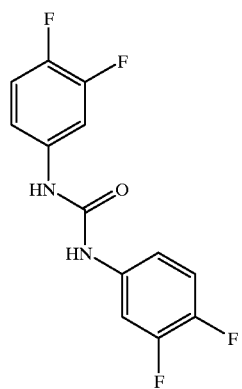 |
| 96 | 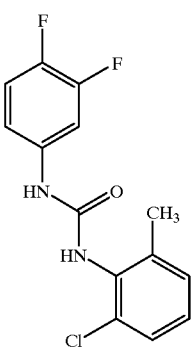 |
-continued
| compound number | Structure |
|---|---|
| 97 | 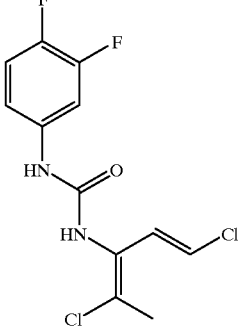 |
| 98 | 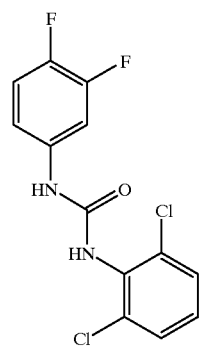 |
| 99 | 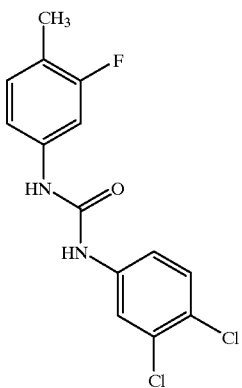 |
| 100 | 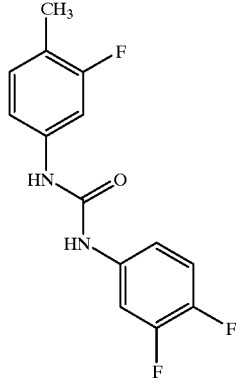 |

-continued

| compound number | Structure |
|---|---|
| 103 | 4-methoxy-2-methylphenyl / 3,4-dichlorophenyl urea |
| 104 | 4-methoxy-2-methylphenyl / 3,4-difluorophenyl urea |
| 105 | 5-chloro-2,4-dimethoxyphenyl / 3,4-dichlorophenyl urea |
| 106 | 5-chloro-2,4-dimethoxyphenyl / 3,4-difluorophenyl urea |

-continued

| compound number | Structure |
|---|---|
| 107 | 2-(carbamoyl)phenyl / 3,4-dichlorophenyl urea |
| 108 | 4-ethoxyphenyl / 3,4-dichlorophenyl urea |
| 109 | 2,4-dimethoxyphenyl / 3,4-dichlorophenyl urea |
| 110 | 2-methylphenyl / 3,4-dichlorophenyl urea |

-continued

| compound number | Structure |
|---|---|
| 111 | 1-(4-methylphenyl)-3-(3,4-dichlorophenyl)urea |
| 112 | 1-(3,4-dichlorophenyl)-3-(3,4-dimethylphenyl)urea |
| 113 | 1-(3,4-dichlorophenyl)-3-(2,5-dimethylphenyl)urea |
| 114 | 1-(4-chlorophenyl)-3-(3,4-dichlorophenyl)urea |

-continued

| compound number | Structure |
|---|---|
| 115 | 1-(4-acetylphenyl)-3-(3,4-dichlorophenyl)urea |
| 116 | 1-(4-ethoxycarbonylphenyl)-3-(3,4-dichlorophenyl)urea |
| 118 | 1-(3,4-dichlorophenyl)-3-(3-methoxy-5-methylphenyl)urea |
| 119 | methyl 2-[3-(3,4-dichlorophenyl)ureido]benzoate |

-continued

| compound number | Structure |
|---|---|
| 120 | 2-fluorophenyl-N'-(3,4-dichlorophenyl)urea |
| 121 | N-(2-ethoxyphenyl)-N'-(3,4-dichlorophenyl)urea |
| 122 | N-(2-chlorophenyl)-N'-(3,4-dichlorophenyl)urea |
| 123 | N-[4-benzamido-2-methoxy-5-methylphenyl]-N'-(3,4-dichlorophenyl)urea |

-continued

| compound number | Structure |
|---|---|
| 124 | 4-chloro-2-[3-(3,4-dichlorophenyl)ureido]benzaldehyde |
| 125 | 5-bromo-2-[3-(3,4-dichlorophenyl)ureido]benzoic acid |
| 127 | methyl 5-chloro-2-[3-(3,4-dichlorophenyl)ureido]benzoate |

-continued

| compound number | Stucture |
|---|---|
| 128 | (structure: methyl 4-chloro-2-[(3,4-dichlorophenyl)carbamoylamino]benzoate) |
| 129 | (structure: 1-(3,4-dichlorophenyl)-3-(2,3-dihydro-1H-inden-5-yl)urea) |

9. A method of treating or preventing a p38-mediated condition, comprising the step of administering an amount of a compound effective to treat or prevent a p38-mediated condition, or a pharmaceutical composition comprising said compound and a pharmaceutically acceptable carrier, to a human or animal in need thereof, wherein the compound has the formula:

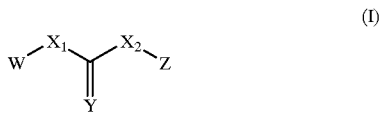

(I)

wherein:
W is an aromatic monocyclic or bicyclic ring system wherein W optionally comprises up to 4 substituents independently selected from $R^1$ and $R^4$;
wherein $R^1$ is halogen, OH, $OR^3$, $NO_2$, $NH_2$, $N(R^3)_2$, $CO_2H$, $CO_2R^3$, $CONH_2$, $CON(R^3)_2$, $COR^3$, $NHCOR^3$, $SO_2NH_2$, $SO_2NR^3$, CN, $SR^3$, 1,2-methyleneoxy, 1,2-ethylenedioxy, phenyl or $CF_3$;
Y is O or NH;
$X_1$ and $X_2$ are $NR^2$;
wherein $R^2$ is selected from H or $C_1$–$C_6$ straight or branched alkyl, $C_2$–$C_6$ straight or branched alkenyl or alkynyl, wherein $R^2$ is optionally substituted with —OH, —$N(R^3)_2$, —Z, —$CO_2H$, —$CO_2R^3$ or —CO—$N(R^3)_2$;
$R^3$ is selected from phenyl, $C_1$–$C_6$ straight or branched alkyl, $C_2$–$C_6$ straight or branched alkenyl or alkynyl, wherein $R^3$ is optionally substituted with halo, —OH, —$OR^4$, —$NO_2$, —$NH_2$, —$N(R^4)_2$, —$CO_2R^4$, —CO—$N(R^4)_2$, —Z, —CN, —$SR^4$, $CF_3$ or —$SO_2NR^4$;
provided that when Y is O and $R^2$ is H, then $R^3$ is not substituted with OH or $NH_2$;
$R^4$ is independently ($C_1$–$C_6$)-straight or branched alkyl, ($C_2$–$C_6$)-straight or branched alkenyl or alkynyl; and Z is selected from monocyclic or bicyclic, aromatic ring systems comprising 5–7 members per ring, and wherein Z optionally comprises up to 4 substituents independently selected from $R^1$ and $R^4$.

10. A pharmaceutical composition comprising the compound according to any one of claims 1 to 8 and a pharmaceutically acceptable carrier.

11. The method according to claim 9, wherein said p38-mediated condition is inflammatory disease, autoimmune disease, destructive bone disorder, proliferative disorder, infectious disease, viral disease, or neurodegenerative disease in a patient.

12. The method according to claim 11, wherein said method is used to treat or prevent an inflammatory disease selected from acute pancreatitis, chronic pancreatitis, asthma, allergies, or adult respiratory distress syndrome.

13. The method according to claim 11, wherein said method is used to treat or prevent an autoimmune disease selected from glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, or graft vs. host disease.

14. The method according to claim 11, wherein said method is used to treat or prevent a destructive bone disorder selected from osteoarthritis, osteoporosis or multiple myeloma-related bone disorder.

15. The method according to claim 11, wherein said method is used to treat or prevent a proliferative disease selected from acute myelogenous leukemia, chronic myelogenous leukemia, metastatic melanoma, Kaposi's sarcoma, or multiple myeloma.

16. The method according to claim 11, wherein
said method is used to treat or prevent an infectious disease selected from sepsis, septic shock, or Shigellosis.

17. The method according to claim 11, wherein said method is used to treat or prevent a viral disease selected from acute hepatitis infection, HIV infection or CMV retinitis.

18. The method according to claim 11, wherein said method is used to treat or prevent a neurodegenerative disease selected from Alzheimer's disease, Parkinson's disease or cerebral ischemia.

19. The method according to claim 9, wherein said p38-mediated condition is ischemia/reperfusion in stroke, myocardial ischemia, renal ischemia, heart attack, organ hypoxia or thrombin-induced platelet aggregation.

20. The method according, to claim 9, wherein said administering results in inhibition of prostaglandin endoperoxide synthase-2.

21. The method according to claim 20, wherein said method is used to treat or prevent edema, fever, analgesia or to manage pain.

22. The method according to claim 21, wherein said pain is selected from neuromuscular pain, headache, cancer pain, dental pain or arthritis pain.

* * * * *